United States Patent
Desain et al.

(10) Patent No.: US 9,084,549 B2
(45) Date of Patent: Jul. 21, 2015

(54) METHOD FOR PROCESSING A BRAIN WAVE SIGNAL AND BRAIN COMPUTER INTERFACE

(75) Inventors: Petrus Wilhelmus Maria Desain, Nijmegen (NL); Jason Farquhar, Nijmegen (NL)

(73) Assignee: Stichting Katholieke Universiteit, Radbound Universiteit Nijmegen, Nijmegen (NL)

(*) Notice: Subject to any disclaimer, the term of this patent is extended or adjusted under 35 U.S.C. 154(b) by 739 days.

(21) Appl. No.: 13/054,239

(22) PCT Filed: Jul. 10, 2009

(86) PCT No.: PCT/NL2009/050421
§ 371 (c)(1),
(2), (4) Date: Mar. 30, 2011

(87) PCT Pub. No.: WO2010/008276
PCT Pub. Date: Jan. 21, 2010

(65) Prior Publication Data
US 2011/0251511 A1    Oct. 13, 2011

(30) Foreign Application Priority Data
Jul. 15, 2008  (NL) .................................. 2001805

(51) Int. Cl.
*A61B 5/04*     (2006.01)
*A61B 5/0484*   (2006.01)
*G06F 3/01*     (2006.01)
*G06K 9/00*     (2006.01)

(52) U.S. Cl.
CPC ............ *A61B 5/04845* (2013.01); *G06F 3/015* (2013.01); *G06K 9/00496* (2013.01)

(58) Field of Classification Search
CPC . A61B 5/04845; G06K 9/00496; G06F 3/015
USPC .................................................. 600/544–545
See application file for complete search history.

(56) References Cited

U.S. PATENT DOCUMENTS

| 5,687,291 A | 11/1997 | Smyth |
| 5,788,648 A | 8/1998 | Nadel |
| 6,349,231 B1 | 2/2002 | Musha |
| 2003/0114886 A1 | 6/2003 | Gluckman et al. |
| 2004/0131998 A1 | 7/2004 | Marom et al. |
| 2005/0182456 A1 | 8/2005 | Ziobro et al. |
| 2005/0283053 A1* | 12/2005 | deCharms ..................... 600/300 |
| 2006/0069635 A1* | 3/2006 | Ram et al. ....................... 705/37 |

FOREIGN PATENT DOCUMENTS

| EP | 1 727 072 A1 | 11/2006 |
| WO | WO 2006/021952 A2 | 3/2006 |
| WO | WO 2008/065239 A1 | 6/2008 |

OTHER PUBLICATIONS

Lalor, et al., "The VESPA: A method for the rapid estimation of a visual evoked potential," NeuroImage 32 (2006) 1549-1561.*

* cited by examiner

*Primary Examiner* — Navin Natnithithadha
*Assistant Examiner* — Eric Messersmith
(74) *Attorney, Agent, or Firm* — Jordan IP Law, LLC; Todd A. Vaughn

(57) ABSTRACT

Method and brain computer interface for processing a brain wave signal of a subject using a brain wave detector. One or more stimuli are applied to the subject which each include a pseudo random noise component. The brain wave signal is detected and mental processing of the one or more stimuli is tracked by correlating the pseudo random noise component and the brain wave signal.

19 Claims, 8 Drawing Sheets

METHOD FOR PROCESSING A BRAIN WAVE SIGNAL AND BRAIN COMPUTER INTERFACE

CROSS REFERENCE TO PRIOR APPLICATIONS

The present application is a National Stage Application of PCT International Application No. PCT/NL2009/050421 (filed on Jul. 10, 2009), under 35 U.S.C. §371, which claims priority to the Netherlands Patent Application No. 2001805 (filed on Jul. 15, 2008), which are each hereby incorporated by reference in their respective entireties.

FIELD OF THE INVENTION

The present invention relates to a method for processing a brain wave signal obtained from a person using a brain wave detector, such as an electro-encephalography (EEG) signal, magneto-encephalography (MEG) signal or electro-corticogram (ECoG) signal. Furthermore, the present invention relates to a brain computer interface and a computer program product.

BACKGROUND OF THE INVENTION

The article 'The brain response interface: communication through visually-induced electrical brain responses", Journal of Microcomputer Applications (1992) 15, 31-45, by Erich E. Sutter discloses an experimental communication system for severely disabled persons that utilizes electrical responses from the brain. This article describes experiments and theories with respect to detection and utilization of visual stimuli, where the stimuli comprise visual patterns displayed on a screen which are rapidly changing in time. The stimuli furthermore comply with a number of requirements and are modulated in time using pseudo-random white binary sequences.

International patent application WO2008/065239 discloses a method to determine the hearing threshold in humans. Specific auditory stimuli and analysis of the related brain response signals are used. The stimuli comprise an auditory signal having a distinct characteristic such as a ramp in frequency or intensity.

U.S. Pat. No. 5,788,648 discloses an EEG apparatus for analysis of quantified stimuli, including calculations of correlations between stimuli and brains signals.

American patent application US2005/0182456 discloses a method of cortical mapping, wherein subcutaneous electrodes are used to generate stimuli directly to brain cell areas, and electromyography is used to measure responses to those stimuli.

International patent application WO2008/025048 discloses a method and device for controlling equipment with the aid of electro-encephalograms (EEG) or electro-corticograms (ECoG). For this, different periodic stimuli are generated, each with a given base frequency. These periodic stimuli (frequency tagged stimuli) can be detected in the EEG or ECoG signals, amongst other by synchronizing the generation of stimuli and detection in the signal processing.

International patent application WO94/17730 discloses thought analysis from brain wave data, such as EEG signals. Use is made of conceptual interpreters, whereby a test subject is presented with conceptual information and background stimuli. The brain wave data is subjected to signal processing using a stimulus model which represents attributes of stimuli.

SUMMARY OF THE INVENTION

The present invention seeks to provide an improved brain wave signal processing, which may be applied to brain computer interfaces for controlling various devices, in which the mental processing of applied stimuli can be detected more reliably.

According to the present invention, a method according to the preamble defined above is provided, in which the method comprises applying one or more stimuli to the person in which each of the one or more stimuli comprises a pseudo random noise component, detecting a brain wave signal, and tracking mental processing of the one or more stimuli by correlating the pseudo random noise component (or a directly related signal such as a derivative) and the brain wave signal. The pseudo random noise component tags the stimulus resulting in a spread spectrum signal. As a result, the detection of the stimulus in the brain wave signal is much more robust and reliable.

In an embodiment, tracing the one or more stimuli is executed for the brain wave signal as detected in a time period after the application of the stimulus. This would allow direct processing and use of the processed signals, e.g. in a brain computer interface application. In other applications, it would also be possible to process longer or repeating stimuli, in order to further improve the robustness of detection.

Tracking mental processing of the one or more stimuli comprises in an embodiment of the present invention transforming the pseudo random noise component, and correlating the brain wave signal and the transformed pseudo random noise component. Transformation may include obtaining a time derivative This allows to reduce the amount of data to be processed. In a further embodiment transforming the pseudo random noise component comprises providing a prediction of a brain wave signal for a specific pseudo random noise component by decomposition of a recorded brain wave signal using contributions associated with rising and falling transitions in the specific pseudo random noise component. By exploiting this characteristic of the pseudo random noise component it is possible to obtain detection results with a high reliability.

In a further embodiment, at least two stimuli are presented to the person with different associated pseudo random noise components, the method further comprising selecting the stimulus with the highest correlation as an indication of selective attention of the test person to the associated stimulus. This embodiment is especially suited for more complex research tasks, and also for brain computer interface applications. In an even further embodiment, the indication of selective attention is used to control a device, such as a mouse, a keyboard, a wheelchair, etc.

The different pseudo random noise components are mutually orthogonal in a further embodiment, and are e.g. a subset chosen from Golden codes. This assures that the stimulus tags are both uncorrelated with themselves over time (i.e. have a low auto correlation), and also uncorrelated with each other (i.e. have low cross correlation), which improves their detectability.

In an exemplary embodiment the one or more stimuli comprises an auditory stimulus. This allows easy implementation of the tagging of the stimulus, and presentation of the stimulus to the test person. E.g. the auditory stimulus is a tone signal (e.g. a saw tooth signal) which is amplitude modulated with a pseudo random noise sequence. The pseudo random noise sequence may be a direct sequence spread spectrum in which the tone is multiplied by a random bit code. As alternatives the stimulus may be in the visual or tactile domain.

In a further embodiment, the brain wave signal is first spatially filtered, e.g. using Independent Component Analysis (ICA) techniques. By using knowledge in which part of the brain the stimulus will be processed, the amount of data to be processed can be reduced, and the reliability can be increased.

In a further aspect, the present invention relates to a brain computer interface comprising a detector for obtaining a brain wave signal from a person, a processor connected to the detector arranged to process the brain wave signal according to any one of the present method embodiments, and a device connected to the processor and arranged to receive processed data from the processor. The device may be a display for presenting processing results, or a device to be controlled by the test person.

In an even further aspect, the present invention relates to a computer program product comprising computer executable code, which when loaded on a computer system arranged to receive data associated with a brain wave signal, provides the computer system with the functionality of any one of the present method embodiments.

BRIEF DESCRIPTION OF DRAWINGS

The present invention will be discussed in more detail below, using a number of exemplary embodiments, with reference to the attached drawings, in which.

DETAILED DESCRIPTION OF THE INVENTION

Figure 1:
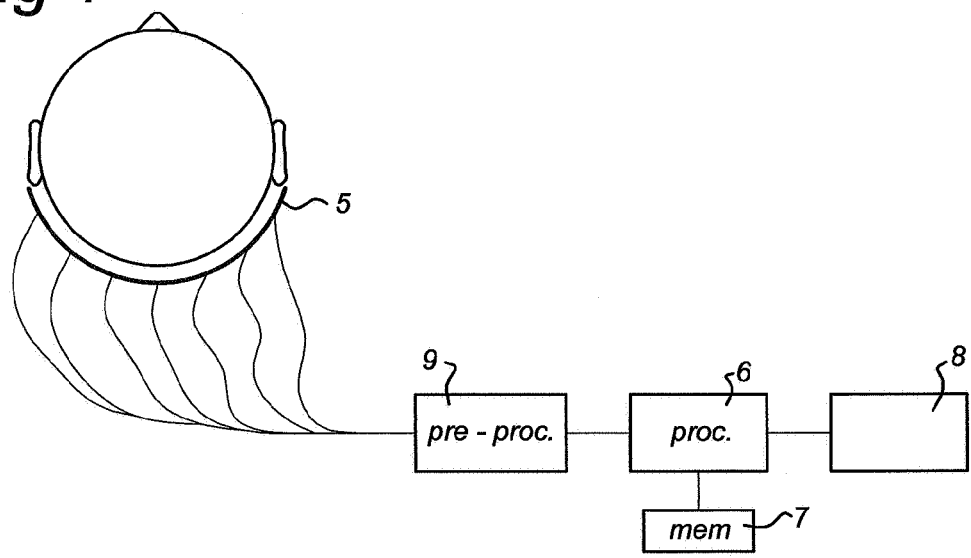
FIG. 1 shows a schematic view of a brain computer interface according to an embodiment of the present invention.

The neural responses of stimuli with a repetitive character have been well studied in electro-encephalography (EEG) and Magneto-encephalography (MEG). These so called Steady State Evoked Potentials (SSEP) are thought to reflect the frequency and phase-locked responses of neural circuits to an incoming periodic stimulation. This has been shown in the tactile, visual, and auditory domain. As certain features of these stimuli, such as power and phase at the stimulation frequency, are modulated by (selective) attention, SSEPs have been used as the basis of brain computer interfaces (BCI). Furthermore, the phase difference between stimulus and response can be exploited as a probe for cognitive processing time and order (modulo the stimulation period). However, interesting frequencies to use for the various domains (in the range of about 10-140 Hz) are in the same range as spontaneous oscillations that occur in the brain (alpha, theta, gamma) and thus stimulus related activity that may complicate analysis.

One approach to attenuating the relatively narrow band noise originating from other cognitive process would be to use a spectrally spread stimulus. One could think of chirps, frequency hopping, pseudo random noise and other signals that have a broadband spectral character. Thus a test with such signal is valuable for the pragmatic aim to increase the robustness of BCI systems.

In this description of embodiments of the present invention, this approach is elaborated for amplitude modulated auditory stimuli and EEG responses. In further embodiments the classification process and a way to structurally decompose the (broadband) noise codes are described and it is demonstrated how they form a powerful new method for probing cognitive processing.

Stimulus tagging is a technique where stimuli are modulated such that the modulation can be detected in neural activity recordings, e.g. brain wave signals such as EEG signals. For example, visual images can be modulated by changing their brightness. This modulation is expected to be processed alongside the stimulus in the brain. Hence, the modulation tags (or watermarks) the stimulus, allowing it to be tracked as it is processed in different brain regions at different time lags. Stimulus tagging is thus extremely useful for basic physiological research. It is also very useful for BCI purposes as selective attention increases the neural response to the selected stimulus, and hence the (detected or processed) strength of that tag.

There are two main types of stimulus tag, steady state tags where the modulation occurs more rapidly than the subject can perceive, and transient tags which happen infrequently and evoke a transient response. Transient effects are widely used in the oddball-type BCIs, such as P300 visual spellers.

Steady state stimulus tags have a number of advantages from a BCI perspective. Firstly, their high frequency means they can potentially give high timing accuracy. Secondly, as they are perceived by the subject as a continuous modulation they can be presented for many modulation cycles, allowing a long integration time which increases the signal-to-noise-ratio such that even very weak responses can be detected.

The most common form of steady state tagging is the frequency tag. Here the stimulus is modulated with a simple repeating modulation, such as a sine wave. A commonly used frequency tag is the Steady State Visual Evoked Potential (SSVEP), the visual type of SSEP as mentioned above. A SSVEP is generated by varying the brightness of a visual stimulus in a sinusoidal fashion. A similar approach using a low frequency amplitude modulation of a higher frequency carrier is the Auditory Steady State Response (ASSR).

Frequency tagging has the advantage that the modulator is concentrated into a very narrow frequency band which is easy to detect using a simple spectral decomposition. Further, because different frequencies are uncorrelated, multiple tags can be used simultaneously and detected with little or no interference.

Despite its advantages, frequency tagging has two potential disadvantages. Firstly, the narrowband nature of the tag leaves it susceptible to interference where a noise source near the tagging frequency can mask the tag. Secondly, the short period of the stimulus may cause aliasing when time lags longer than the repetition period become indistinguishable from shorter lags.

According to the present invention a novel alternative steady state stimulus tagging technique is used, called noise tagging. The main idea is to spread the tagging signals' power over a wide range of frequencies instead of focusing it all in a narrow band. This spreading has the advantage that losing one particular part of the signal spectrum has little effect on signal detectability. In fact the reduction in signal detectability is roughly linear with the fraction of the signal spectrum lost.

Such interference robustness is important for BCI/neuro-scientific applications where parts of the signal are likely to be lost due to either external (or neural) noise effects or simply because they are filtered out during cognitive processing. By using spread spectrum techniques the chance that some signal always remains in the recorded activity is maximized. Note, this also means the tag is robust to inter-subject variations in stimulus response.

Noise tagging has the additional advantage that the tagging signal has a much longer period, e.g. about 1.5 s. This is much longer than the neural processing lags that are likely to occur so temporal aliasing is no longer a problem.

In an exemplary embodiment of a detection system exploiting noise tagging, a detector 5 is positioned on the scalp of a test person, as shown in the schematic view of FIG. 1. The detector 5 is used to obtain the brain wave signal, e.g. an EEG signal, using a pre-processor 9 which includes amplifiers, filters and/or analog to digital converters as known in the art for obtaining a brain wave signal. The brain wave signal is fed to a processor 6, such as a general-purpose computer, or a dedicated signal processor. The processor 6 is connected to a memory unit 7 (e.g. a hard disk) for storing intermediate data during signal processing and for storing instructions for the processor 6. Also, the processor 6 may be connected to a further apparatus 8, such as a display for showing the processing results, or a system or device to be controlled by the test person. E.g. this may be implemented as a Brain Computer Interface (BCI), in which control signals to a system or device 8 are generated based on the measured brain wave signal (e.g. by detecting to which of two stimuli the test person's attention is directed).

The processor 6 is arranged to perform any one of the method embodiments described using the proper input and output signals. The method embodiments may also be implemented as a computer program, e.g. stored on a computer program product such as an optical disc or on the memory unit 7, comprising computer executable code or instructions. When the computer program is loaded on a generally known computer system having the appropriate interfaces (e.g. to detector 5 or pre-processor 9), the functionality of the method embodiments is obtained.

In an embodiment, a Direct Sequence (DS) spread spectrum is used. In this DS method a random "spreading code" is multiplied with the signal to spread its power over a wide band. In theory, a purely random process can be used to generate the spreading code. However, this can cause problems if the generated tag happens to repeat (i.e. be highly correlated with) itself at some point—re-introducing the temporal aliasing problem. Further, if one wishes to use more than one noise tag at the same time, it is hard to guarantee that they will be uncorrelated.

These problems have been solved (e.g. in the telecommunications literature) using specially designed pseudo random number generators. As an example a particular form of these pseudo random codes are used, i.e. Golden codes, to ensure that the different noise tags are maximally uncorrelated in time with themselves (i.e. have low auto-correlation) and each other (i.e. have low cross-correlation). Using this approach, firstly interference with other noise tags is minimized, and thus multiple tags can be used at the same time, e.g. in a selective parallel attention BCI. Secondly, temporal aliasing is minimized, and thus neuronal processing lags can be determined accurately.

When examining brain wave signals detected when exposed to pseudo random noise tagged stimuli, looking at the power in a single spectral band is not sufficient, and therefore detecting spread-spectrum tags is a little more complex than for frequency tagging. However, under the assumption that the brain response is an attenuated, time-lagged version of the stimulus the noise-tag can be detected using a simple correlation approach.

In an embodiment thereof, the tagging signal can be 'shifted' over the brain data until the time lag where they have maximal correlation is found. In a further embodiment, e.g. if it is assumed that the brain is responding to some more complex linear transformation of the tag (such as its first derivative) then more advanced techniques can be used. The signal processing can be performed on the directly obtained brain wave signal (usable for BCI applications), or signal processing may be applied on a plurality of samples e.g. obtained in a number of experiments relating to the same stimulus. For research purposes, the samples may even be obtained from different test subjects.

Figure 7:
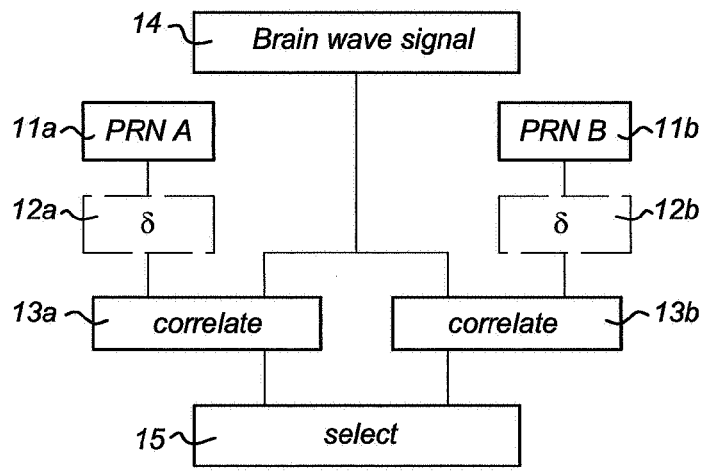
FIG. 7 shows a flow diagram of an embodiment of the present method for processing a brain wave signal.

This is shown schematically in the flow diagram of FIG. 7 in which two possible stimuli A and B are used in a test set-up. The pseudo random noise components A and B (indicated by reference numerals 11a and 11b, respectively, are used as input to correlation calculating blocks 13a and 13b, as well as the detected brain wave signal 14. In an alternative embodiment, a transformation of the pseudo random noise components A and B is performed before the correlation calculation, e.g. a first time derivative δ as indicated in functional blocks 12a and 12b in FIG. 7. The separate correlation results are compared in functional block 15, and the highest correlation score indicates which of the stimuli is most likely presented to the person and present in brain wave signal 14. Although this embodiment refers to the use of two stimuli, more than two stimuli may be used and processed as described.

In a further embodiment of the present invention, a more advanced technique is used which relates to the use of decomposition of the EEG response to the first-derivative of the pseudo random noise component in the stimulus tag, which as will be demonstrated below gives impressive results.

Figure 8:
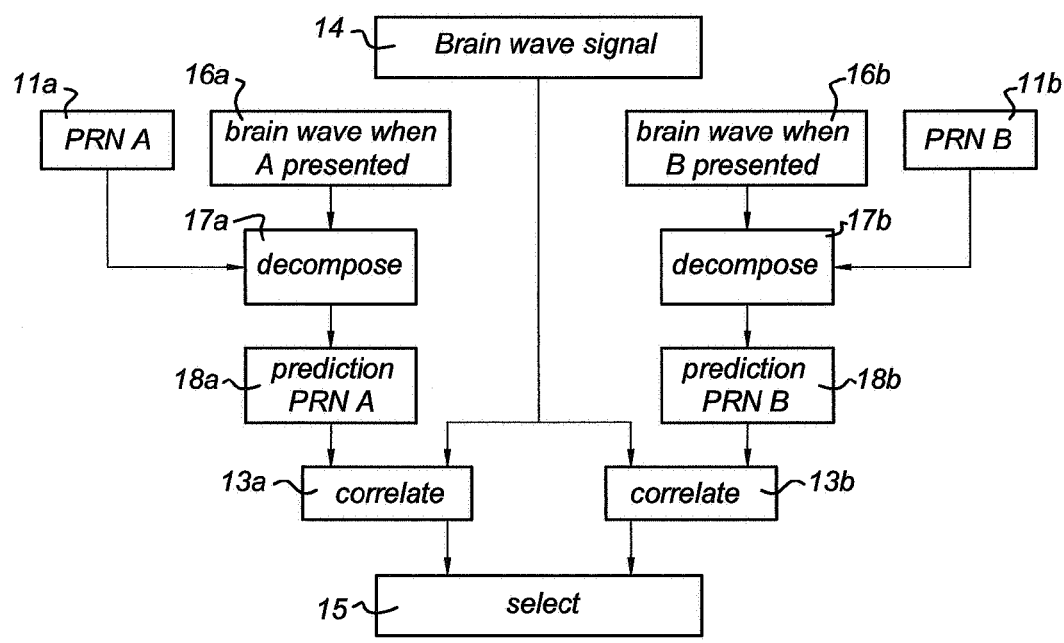
FIG. 8 shows a flow diagram of a further embodiment of the present method for processing a brain wave signal.

In FIG. 8 a flow diagram is shown in which this embodiment is implemented. Again, the brain wave signal 14 as detected is input to two correlation functions 13a, 13b. However, in this embodiment, the other input of the correlation functions 13a, 13b is a transformed version of the pseudo random noise components 11a, 11b. A recorded brain wave signal 16a, 16b is decomposed in respective decompose functions 17, 17b using the available information on specific characteristics of the pseudo random noise component 11a, 11b. In this manner, a prediction 18a, 18b of a brain wave signal to be expected in response to a specific pseudo random noise component is obtained, and subsequently used in the correlation functions 13a, 13b. Again, a selection is made in functional block 15, and the most likely candidate to which the person's attention is directed is selected. Although this embodiment refers to the use of two stimuli, more than two stimuli may be used and processed as described.

The relevant aspects of the signal that can be found back in the response depend only on the rising (0-1) and falling (1-0) transitions. It is further assumed that each transition contributes a time-limited waveform in the EEG response. A last assumption is that the contributions from each edge combine linearly into the full EEG. In algebraic terms a model can be defined as:

$$x(t) = \sum_{\tau=1}^{L} I_r(t) r(t-\tau) + I_f(t) f(t-\tau)$$

where, x(t) is the modeled EEG response at time t, L is the duration of the response, r(.),f(.) are the temporal responses of the brain to a rising and falling edge in the stimulus, respectively, and $I_r(t)$, $I_f(t)$ are indicator functions which have the value 1 if there is a rising/falling edge at time t, and 0 otherwise.

This model can more succinctly be expressed in matrix notation using a structure matrix M to encode the indicator functions $I_r$, $I_f$, as $$x = \left[ \begin{array}{c} \vdots \\ I_r(i \ldots i+L) \\ \vdots \end{array} \middle| \begin{array}{c} \vdots \\ I_f(i \ldots i+L) \\ \vdots \end{array} \right] \left[ \begin{array}{c} r \\ f \end{array} \right] = Mp$$

where x is the column vector of modeled response for each time, the rows of M signify sample times with each row being the previous row shifted one element to the right, and p is the concatenation of the two types of response functions r, f This equation is linear in the temporal responses, r and p. Now it is possible to find the parameters using a least-squares regression with the measured averaged EEG response.

Figure 2:
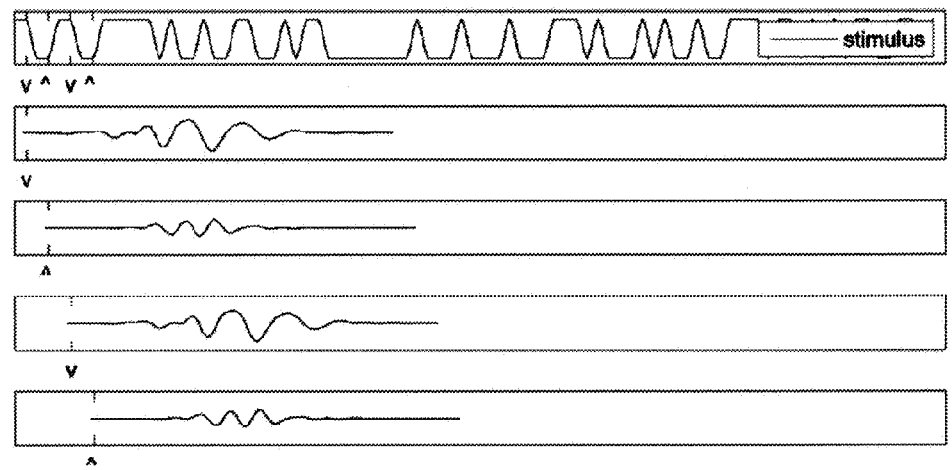
FIG. 2 shows a plots of noise tagged stimulus and the decomposition of the associated responses in a brain wave signal.
Figure 2:
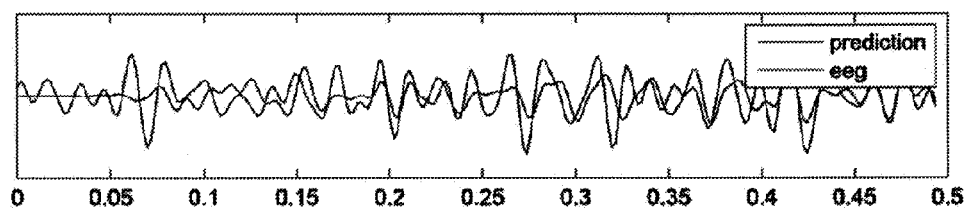

The graphs shown in FIG. 2 illustrate this method. The first two rising and falling edges in the pseudo random noise modulated signal are indicated using the symbol ˆ for a rising edge and for a falling edge. In the graphs below the response signal for each of the rising and falling edges is given (as Event Related Potential, ERP). In the lower graph of FIG. 2 the summation of these responses is shown, as well as the actual measured EEG signal in response to the auditory stimulus.

Figure 3:
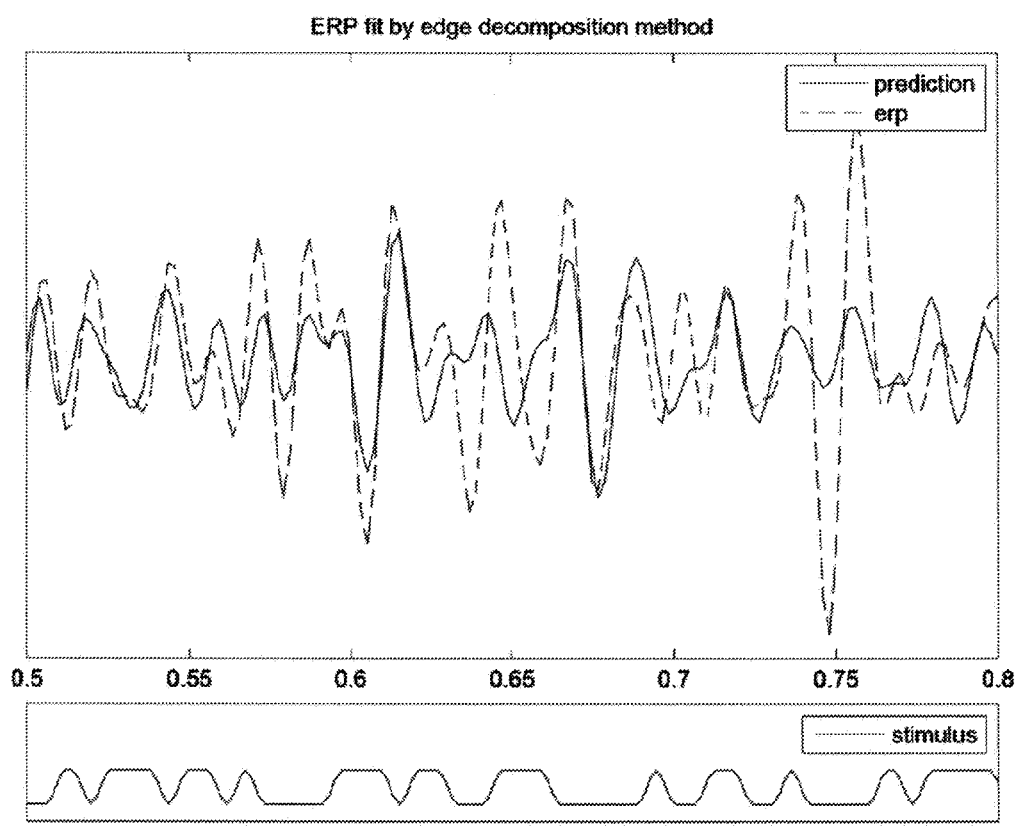
FIG. 3 shows a fitting of an event related potential using an embodiment of the present invention.

The decomposition was conducted for each channel of the EEG signal. This yielded very good fits: predictions explained up to 33% in more than 1600 ERP samples, using 200 parameters. The fit between predicted and measured ERP can be appreciated by eye from the graphs shown in FIG. 3.

EXAMPLE

The EEG responses were collected for 140 trials of listening to a saw-tooth carrier wave of 420 Hz, amplitude modulated by one of two cosine filtered pseudo random noise modulators presented at 168 bits/second.

To test the effectiveness of the noise-tagging approach a series of EEG based auditory perceptual and selective attention experiments were conducted. The aim of these experiments is to test if the noise tag is detectable in the EEG, to compare its performance with pure frequency tagging, and to see if selective attention to noise tagged stimuli can be used as the basis for a BCI.

In detail the experimental design is:
a saw-tooth tone of 420 Hz is used as a carrier;
tags are applied to these tones using binary amplitude modulation, where for a binary zero the amplitude is reduced to 20% of its original value;
two frequency tags at 42 and 70 Hz (for comparison with the noise tag);
two noise tags, called tag A and B, both 255 bits long with a 168 bit/s modulation rate, (≈1.5 s noise tagging period);
a single tag was used for each epoch of 3 s, i.e. 2 noise tag periods.

two tasks are used:
Perceptual—where only a single carrier and tag is used,
Serial Selective Attention—where the subject selectively attends (by counting) to one of the tags, which are presented in a random order.

In a further embodiment also a Parallel Selective Attention task is possible, where two (or even more) carriers and tags are presented simultaneously (e.g. one to each ear), and the subject will be instructed to attend selectively to either the left or the right stimulus. In this embodiment the stimuli will differ in both pitch and spatial location.

Figure 4:
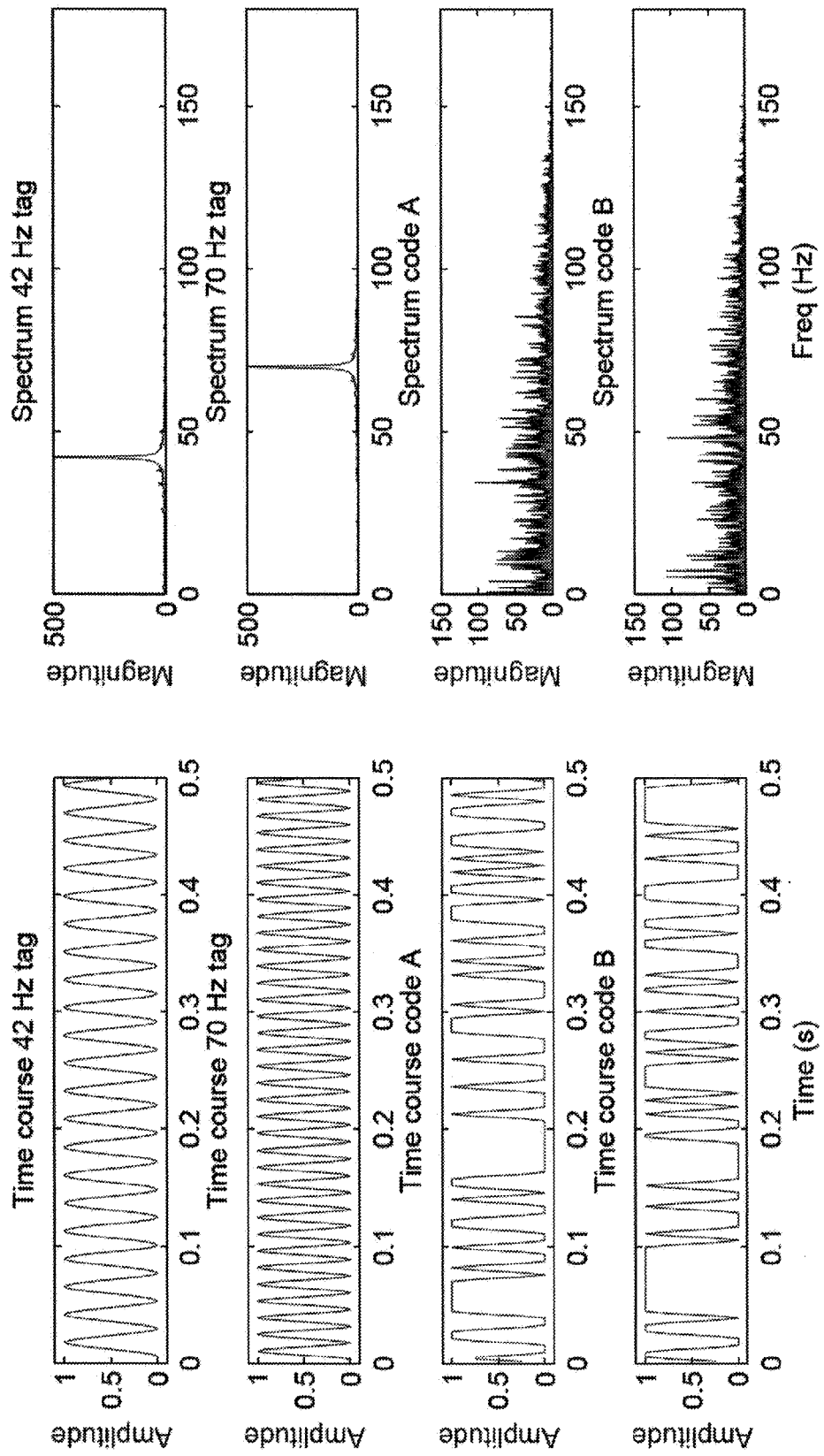
FIG. 4 shows time and frequency domain plots of tagged stimuli used in an experiment.

An example of auditory noise-tags and frequency tags used for this example and the associated spectra are shown in FIG. 4. On the left side, the time courses are shown of the amplitude modulated sequences. On the right side, the spectral distributions of the corresponding tags are shown, which clearly show the spread spectrum nature of the noise tags A and B.

The experiments took place in an acoustically and electrically isolated room, with an EEG signal recorded in a 128 electrode Biosemi active electrode system sampled at 2048 Hz (though for analysis this was down sampled to 512 Hz).

Figure 5:
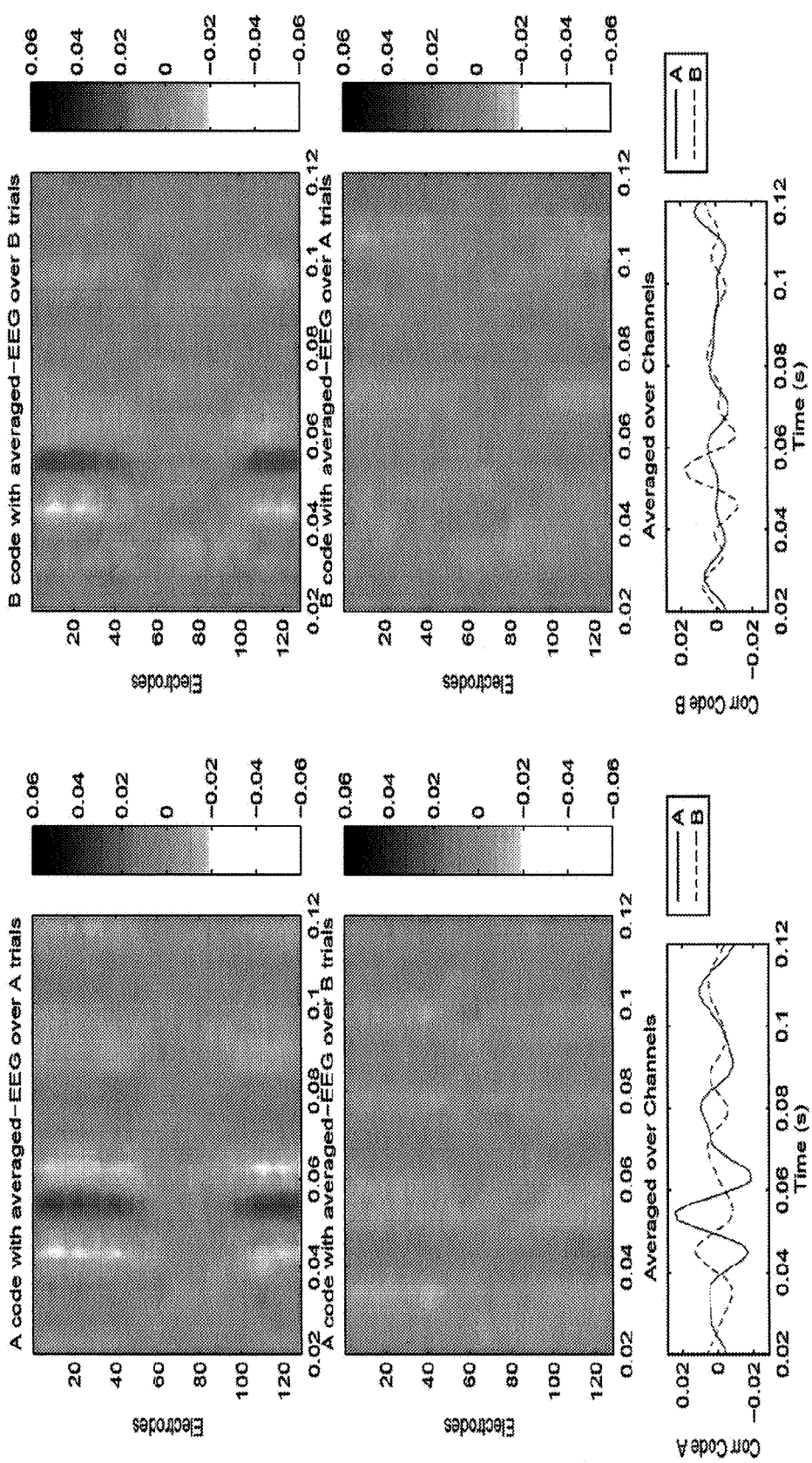
FIG. 5 shows plots of correlation analysis of the tagged stimuli as shown in FIG. 4.

In. FIG. 5, the correlation analyses are shown for the perceptual task described above. The plots show the correlation coefficient computed between the noise tag and the EEG signal (band-passed between 30-80 Hz) on a channel-by-channel basis. On the left side, the correlation of the A tag with the EEG, for each channel and time averaged over A tagged epochs (top row), over B tagged epochs (middle row) and for each time averaged for all channels and for the different sub-sets of epochs (bottom row). On the right side, similar plots are shown with the tags A and B reversed. These results show that the noise tag is indeed identifiable in the EEG signal using the correlation method. Also, the neural processing lag can be identified (50 ms in this case). Further, which of the two noise tags was used can also be seen easily. Initial analysis is also promising showing a definite attentional effect, with the attended tag having a stronger response.

In a further embodiment, a simple correlation approach may be used to classify EEG signals, wherein the predicted class is that class which has maximal correlation with its class prototype. Note this correlation is computed over a sub-set of the electrodes of the detector 5, where this sub-set is determined during training by a step-wise forward selection process.

Results for two types of class-dependent prototypes are given now, the first is the predicted EEG based upon decomposition approach presented above, the second is simply the mean EEG response for this class. This second prototype is used as a baseline to demonstrate the power of the decomposition approach.

The decomposition approach treats all rising and falling edges as the same and so cannot represent any non-linearity or history dependence of the response. However, because it uses an order of magnitude fewer parameters, the decomposition may extract underlying regularities better and is less prone to over fitting.

All classification results are estimated using three seconds of EEG data with 10-fold cross validation, with 20 testing trials, from a dataset containing 280 trials (140 per class). An even further embodiment with improved performance comprise the use of Independent Components Analysis (ICA) to spatially filter the data before decomposition.

ERP template matching yields a 79% correct score, using all 128 channels. The composed predictions yielded a classification rate of 85%. Preprocessing the data with ICA gave a performance 94% (using on average 9 ICA components).

Figure 6:
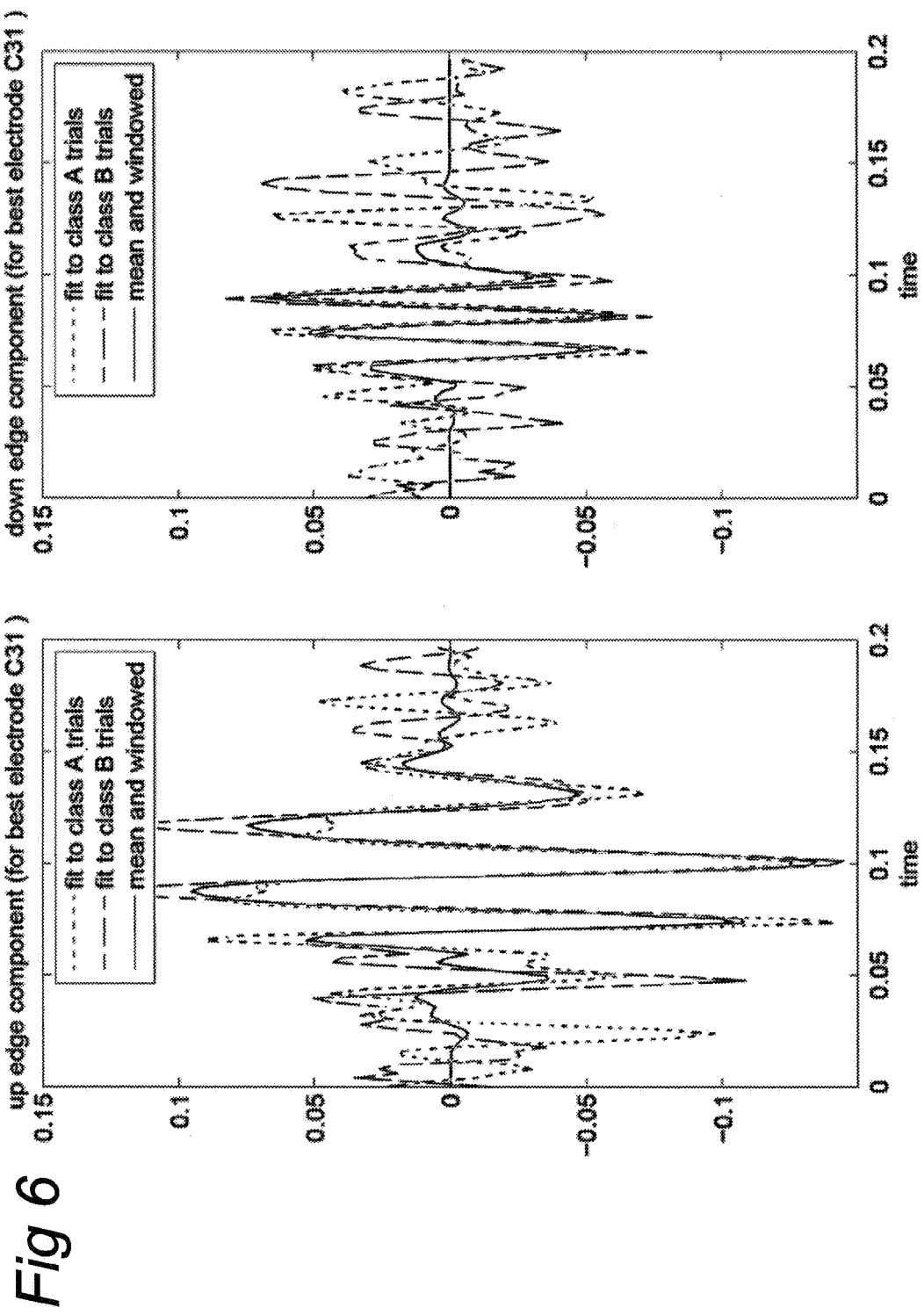
FIG. 6 shows plots of rising and falling components of fits to the noise tagged stimuli of FIG. 4.

In FIG. 6 the edge waveforms are shown for the two classes A and B. It can be seen how the responses are similar in the central region but differ towards the edges. In an embodiment, it is assumed that these differences are due to over fitting, and a simple cosine window (parameters) and the mean of the two waveforms are used to suppress these differences, which is shown in FIG. 6 as the averaged and windowed waveform used for classification. Note that the use of an appropriately regularized parameter estimate may be a better approach to deal with this over fitting issue.

In further analysis it was shown that indeed the wide band character of the noise tag enables detection when part of the signal is distorted or removed.

Furthermore, it was found that classification performance reduces with different decreasing trial duration. The bit rate exhibits an optimum at around 1 second trials.

To further validate the claim that the use of training sets for each code is unnecessary, classification rates were collected by training the edge decomposition only by the other code. Thus each code was detected, using only data (edge waveforms) derived from the other class. Classification rates only dropped by only a few percent (from 94 to 91). This limits the amount of time needed for collecting training data in multi-class setups considerably, and would never be possible in another approach that uses induced or evoked responses directly.

Another advantage of the present method embodiments is that a response is fitted to each rising or falling edge. As each training trail contains many rising and falling edges, very few trials are necessary to produce reliable estimates.

The experimental design used where the subject must count either the noise tag or the intervening frequency tagged stimuli, also allows to preliminary investigate the effect of attention on the response. Attentional modulation is necessary to use this method to form the basis of a BCI. Such an effect is apparent, with attended trials having a slightly higher correlation than for the non-attended trials.

Using the present embodiments, as described above, it is possible to exploit pseudo random noise components with certain characteristics as a stimulus tagging method. Furthermore, the EEG response can be predicted from a decomposition based on the structure of rising and falling edges in the tag. For auditory amplitude modulation this decomposition technique proved very successful: classification rates are high and can be reached with very little data, and even from data obtained from a different tagging sequence. Furthermore, the detection is robust with shorter durations or small pass bands causing a slow and graceful degradation of the classification rate. These properties show that noise tagging is also possible as the basis for a BCI. It is usable in the tactile and visual domain as well.

Figure 9:
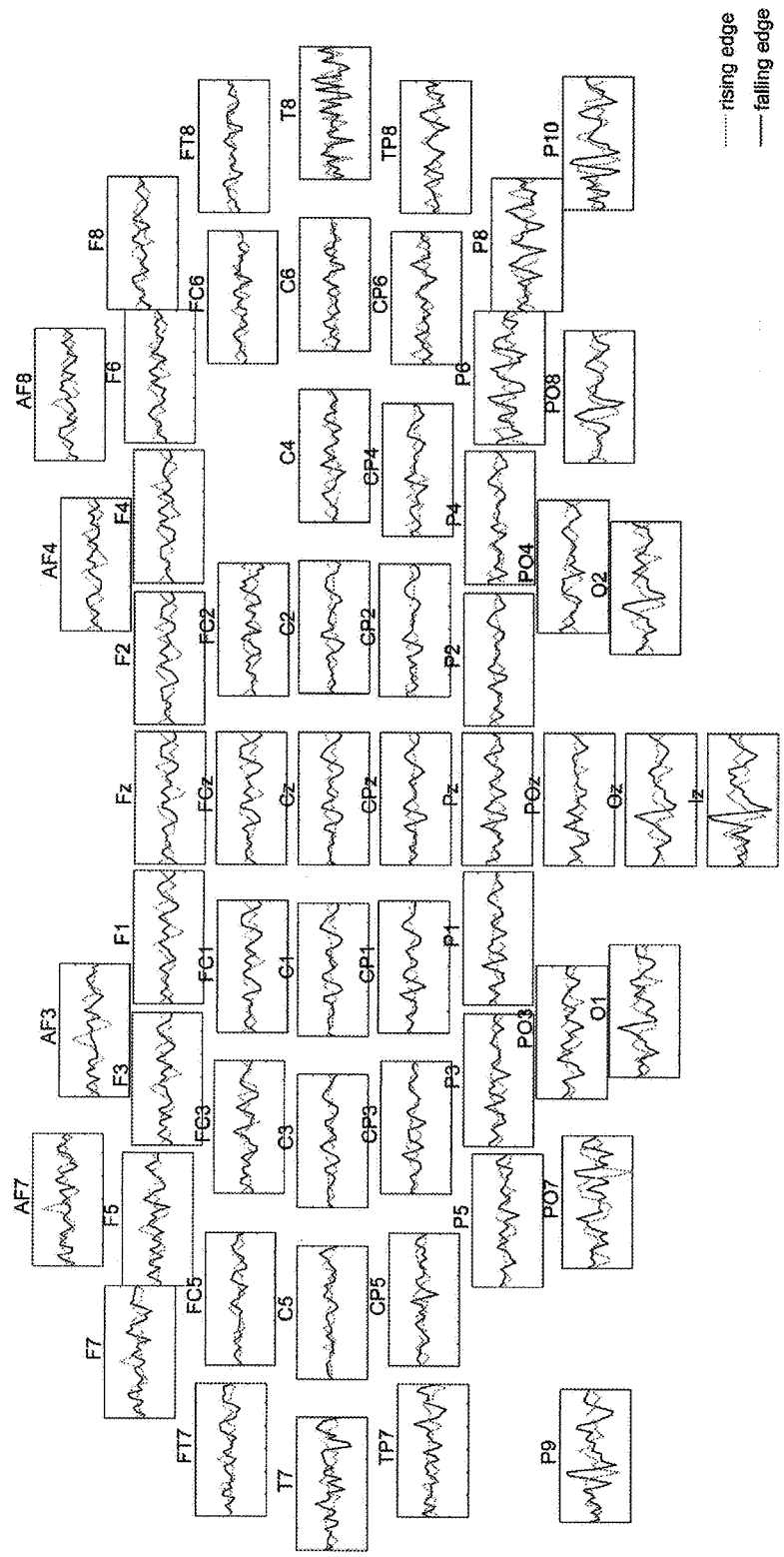
FIG. 9 shows plots of brain signals detected during a noise-tagging test with visual stimuli.
Figure 10:
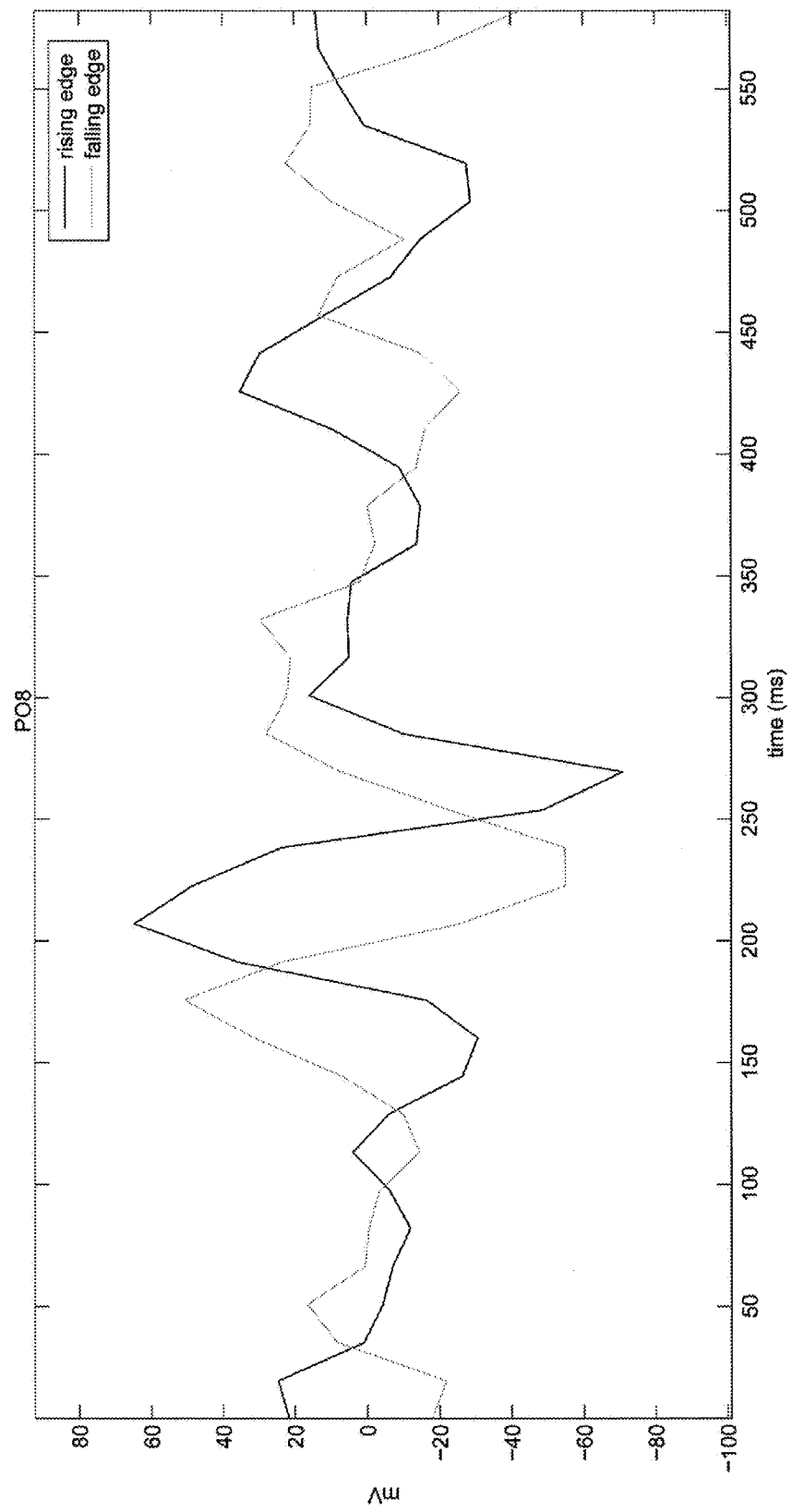
FIG. 10 shows a plot of one electrode signal of the plots of FIG. 9.

In a further experiment visual noise-tagging was applied using the embodiments described earlier. The plots in FIGS. 9 and 10 show the results of the deconvolution/decomposition algorithm applied to the data collected for various electrode positions. In the processing of the data the impulse response for the rising and falling edges only was deconvolved. It was shown that this method seems to work in that it was possible to get 11/15 letter correct prediction using this technique, which is quite good.

In FIG. 9 the results for all the electrodes used in the experiment are shown. It can be seen that the response is maximal in the occipital region (at the bottom of the figure) which corresponds to the visual processing region of the brain. There is also a strong response at the frontal region (top of the figure) which is where the eyes are, which is again what one would expect for a visual input.

FIG. 10 shows a 'zoomed in' version of the plots of FIG. 9, focused on the electrode labelled P08. This electrode is at the back of the plot and showed the nicest response to the stimulus. From this plot it is clear that the responses to the rising and falling edges are roughly the same, except for a difference in the time lag of the response.

In a further embodiment, pseudo random bit codes are used as noise tags, which preserve their low auto and cross correlation properties when short sub-sequences are used.

Although the present invention has been described in detail using an embodiment in which EEG signals are processed, the present method and system may also be used when the brain wave signal comprises MEG signals, or ECoG signals (ElectroCorticograms). The detector 5 may be adapted to detect the associated brain wave signals from the human brain of the test person.

What is claimed is:

1. A method for processing a brain wave signal obtained from a person using a brain wave detector, the method comprising:
   applying at least one stimuli to the person, wherein each of the at least one stimuli comprises a spread spectrum pseudo random noise component;
   detecting a brain wave signal; and then
   tracking mental processing of the at least one stimuli by correlating the spread spectrum pseudo random noise component and the brain wave signal,
   wherein tracking of the at least one stimuli comprises:
   transforming the spread spectrum pseudo random noise component by providing a prediction of a brain wave signal for a specific spread spectrum pseudo random noise component by decomposition of a recorded brain wave signal using contributions associated with rising and falling transitions in the specific spread spectrum pseudo random noise component; and
   controlling a device based on said prediction of the brain wave signal.

2. The method of claim 1, wherein tracking mental processing of the at least one stimuli is executed for the brain wave signal as detected in a time period after application of the at least one stimulus.

3. The method of claim 1, wherein at least two stimuli are presented to the person with different associated spread spectrum pseudo random noise components.

4. The method of claim 3, further comprising selecting one of the at least one stimulus with the highest correlation as an indication of selective attention of the person to the associated stimulus.

5. The method of claim 4, wherein the indication of selective attention is used to control a device.

6. The method of claim 4, wherein the different spread spectrum pseudo random noise components are mutually orthogonal.

7. The method of claim 1, wherein the at least one stimuli comprises an auditory stimulus.

8. The method of claim 7, wherein the auditory stimulus is a tone signal amplitude modulated with a pseudo-random noise sequence.

9. The method of claim 1, wherein the brain wave signal is first spatially filtered.

10. A brain computer interface comprising:
   a detector for obtaining a brain wave signal from a person;
   a processor connected to the detector and arranged to process the brain wave signal by:
   applying at least one stimuli to the person, wherein each of the at least one stimuli comprises a spread spectrum pseudo random noise component;

detecting the brain wave signal; and tracking mental processing of the one or more stimuli by correlating the spread spectrum pseudo random noise component and the brain wave signal, wherein tracking the at least one stimuli comprises transforming the spread spectrum pseudo random noise component by providing a prediction of a brain wave signal for a specific spread spectrum pseudo random noise component by decomposition of a recorded brain wave signal using contributions associated with rising and falling transitions in the specific spread spectrum pseudo random noise component, and a device connected to the processor and arranged to receive processed data from the processor.

11. The brain computer interface of claim 10, wherein the processor is arranged to execute tracking mental processing of the at least one stimuli for the brain wave signal as detected in a time period after application of the at least one stimuli.

12. The brain computer interface of claim 10, wherein at least two stimuli are presented to the person with different associated spread spectrum pseudo random noise components.

13. The brain computer interface of claim 12, wherein the processor is further arranged to select one of the at least one stimuli with the highest correlation as an indication of selective attention of the test person to the associated stimuli.

14. The brain computer interface of claim 13, wherein the indication of selective attention is used to control the device.

15. The brain computer interface of claim 13, wherein the different spread spectrum pseudo random noise components are mutually orthogonal.

16. The brain computer interface of claim 10, wherein the at least one stimuli comprises an auditory stimulus.

17. The brain computer interface of claim 16, wherein the auditory stimulus is a tone signal amplitude modulated with a pseudo-random noise sequence.

18. The brain computer interface of claim 13, wherein the processor is further arranged to first spatially filter the brain wave signal.

19. A computer program product having computer executable code stored on a non-transitory computer readable medium, the computer program product comprising:

code arranged to receive a brain wave signal;

code arranged to process the brain wave signal by:

applying at least one stimuli to the person, wherein each of the at least one stimuli comprises a spread spectrum pseudo random noise component;

detecting the brain wave signal; and tracking mental processing of the one or more stimuli by correlating the spread spectrum pseudo random noise component and the brain wave signal, wherein tracking the at least one stimuli comprises transforming the spread spectrum pseudo random noise component by providing a prediction of a brain wave signal for a specific spread spectrum pseudo random noise component by decomposition of a recorded brain wave signal using contributions associated with rising and falling transitions in the specific spread spectrum pseudo random noise component.

* * * * *